(12) United States Patent
Oreper et al.

(10) Patent No.: US 6,272,936 B1
(45) Date of Patent: Aug. 14, 2001

(54) PRESSURE SENSOR

(75) Inventors: Boris Oreper, Newton; John Brenneman, Bellingham, both of MA (US)

(73) Assignee: Tekscan, Inc, South Boston, MA (US)

( * ) Notice: Subject to any disclaimer, the term of this patent is extended or adjusted under 35 U.S.C. 154(b) by 0 days.

(21) Appl. No.: 09/027,129

(22) Filed: Feb. 20, 1998

(51) Int. Cl.$^7$ ....................................................... G01L 1/04
(52) U.S. Cl. ........................................... 73/862.621
(58) Field of Search ...................... 73/862.621, 862.626, 73/862.628, 862.041–862.043

(56) References Cited

U.S. PATENT DOCUMENTS

| | | | |
|---|---|---|---|
| 4,734,037 | 3/1988 | Maness et al. | 433/68 |
| 4,856,933 | 8/1989 | Maness et al. | 433/68 |
| 5,033,291 | 7/1991 | Podoloff et al. | 73/172 |
| 5,086,652 | 2/1992 | Kropp | 73/767 |
| 5,159,159 | * 10/1992 | Asher | 178/18 |
| 5,170,663 | 12/1992 | Kovacevic | 73/379 |
| 5,222,399 | 6/1993 | Kropp | 73/862.68 |
| 5,505,072 | 4/1996 | Oreper | 73/4 |
| 6,006,386 | * 12/1999 | Mohaupt | 73/862.68 |

* cited by examiner

Primary Examiner—Benjamin R. Fuller
Assistant Examiner—Jewel V. Thompson
(74) Attorney, Agent, or Firm—Wolf, Greenfield & Sacks, P.C.

(57) ABSTRACT

A novel pressure sensor mechanism is provided which includes both a novel pressure sensor assembly and a novel handle for use therewith. The pressure sensor assembly has at least one pressure sensor at its distal end, the pressure sensor having electrodes which are connected through spaced leads to output terminals at a proximal end of the assembly. Even though sensor electrodes and leads may be on facing substrate sections of the assembly, the assembly is designed so as to permit all output terminals to be electrically accessed from the same side of the sensor assembly. An additional output terminal may be provided for preferred embodiments, which terminal is accessible from the same side of the sensor assembly as the other two output terminals, is substantially smaller than the other two output terminals and is connected to one of the other two output terminals by a sensor-ok lead or trace. The handle has a circuit board with a terminal corresponding to each output terminal on the sensor assembly, and a slot for receiving the proximal end of the sensor assembly and for aligning such assembly with each of its output terminals adjacent the corresponding terminal on the circuit board. The handle also includes a member for applying pressure to the side of the sensor assembly opposite the output terminals and a mechanism for permitting such pressure to be released so as to facilitate insertion and removal of the sensor assembly from the handle. The handle also includes controls which operate in conjunction with the sensor-ok trace on a sensor assembly to detect when good electrical contact is being made between the terminals of the sensor assembly and the corresponding terminals of the handle circuit board, and for receiving and suitably outputting pressure measurements from the sensor.

10 Claims, 7 Drawing Sheets

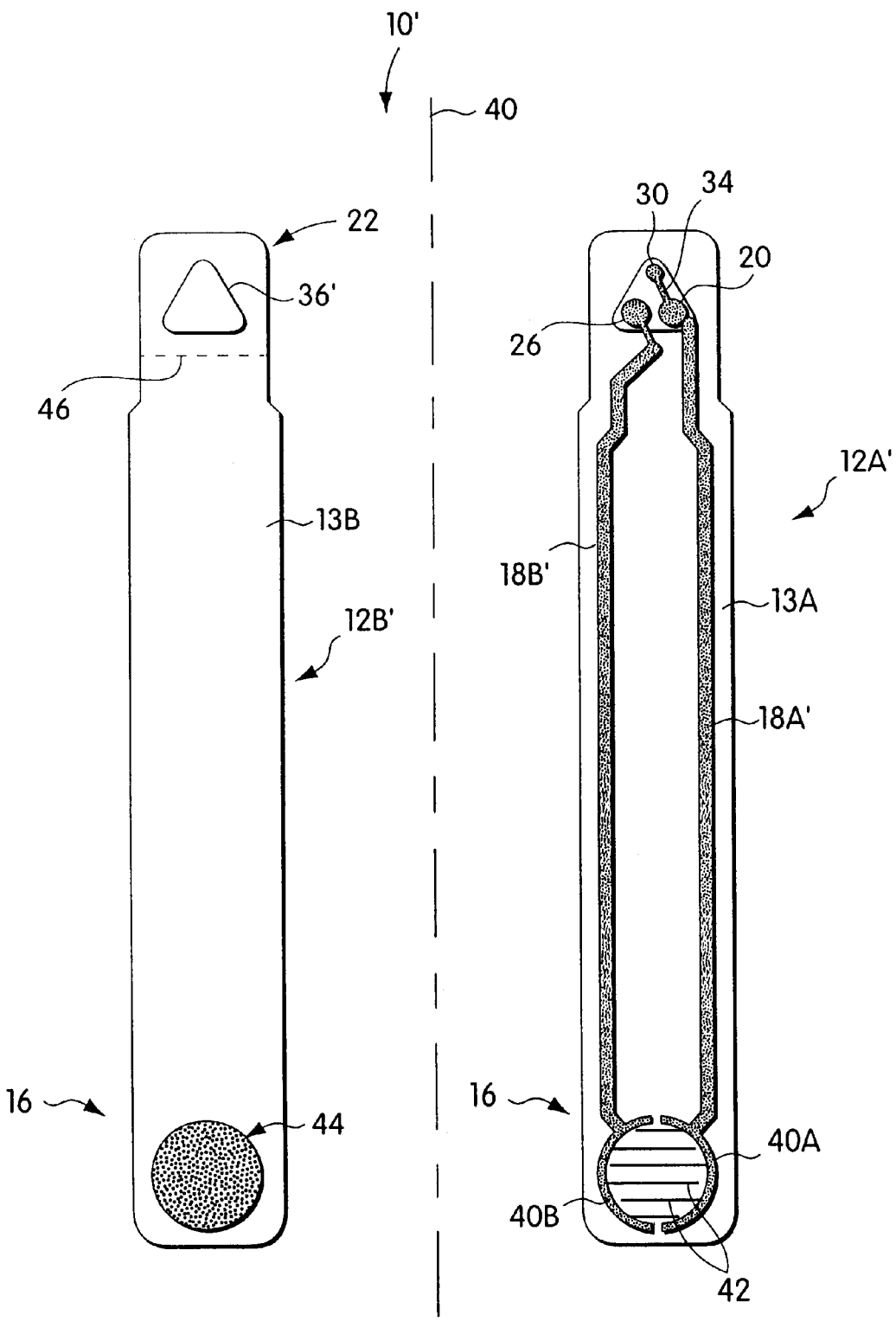

PRESSURE SENSOR

FIELD OF THE INVENTION

This invention relates to pressure sensors and more particularly to flexible pressure sensor assemblies and to handles for use with such assemblies.

BACKGROUND OF THE INVENTION

There are many applications where a need exists to detect pressure between two contacting surfaces, either at a single point, or at a plurality of points so as to provide a pressure profile. Such applications include detecting pressure at gaskets, seals, and other contacting surfaces in various industrial equipment for alignment, adjustment, various other set-up functions, testing, maintenance, and the like; in research facilities for measurement and testing of various products; and in medical facilities for measuring and testing such things as foot pressure distribution, dental occlusion and the like. While pressure sensors for certain of these applications are fabricated as a matrix array, many of these applications require only one or more button sensors, the output or outputs from which are read locally, are fed to a computer, either directly or indirectly, or are otherwise utilized.

In order to achieve optimum sensitivity for a given application, it is desirable that the sensor utilized be selected so as to function optimally in the pressure range being measured. Thus, where the pressure range over which measurements are being taken is small, and detection of small pressure changes is desired, high sensitivity sensors are required; while where the pressure range extends over many pounds or kilograms, sensitivity at the ounce or gram level may be more than adequate. Further, while the sensor elements interposed between the contacting surfaces for which pressure is being measured are high wear items which may only be suitable for a single test or a small number of tests, the remainder of the equipment may have an extended lifetime. Therefore, it is desirable to design sensor equipment with low-cost, flexible pressure sensor assemblies having various configurations and sensitivities which can be easily inserted and removed from a handle which may be connected directly or indirectly to a computer receiving the measurements, or may otherwise output the measurements. While the handle is generally little more than a connector to the pressure sensor assembly, it may, in some applications, also contain selected circuitry. For example, since the output from the sensors may be at relatively low voltage and/or current, the handles for the sensor assembles may contain amplifiers for such signals. Further, since analog output signals are subject to distortion, such handles may also contain converters for changing analog outputs from the sensors to digital signals applied to the computer and for converting digital control signals from the computer to analog. For example, the computer may control the test voltage applied to the sensor(s) to control sensitivity.

One problem with such handles is assuring that the sensor is properly seated in the handle before measurements are taken, since improper seating of the sensor in the handle can result in either erroneous readings being taken or in a loss of data which may be difficult to subsequently reconstruct. Two factors contribute to and insure proper seating has occurred before measurements are taken. The first factor is to design the sensor and handle such that the sensor may be easily inserted and removed while still assuring that, when in use, sufficient pressure is applied against the sensor assembly to assure good electrical contact between its terminals and those of the handle. The second factor is to provide a simple way of detecting good electrical contact between sensor assembly and handle terminals and of providing feedback to the user or operator that good electrical contact has been established before a sensor assembly is used to take measurements. If the user does not obtain such feedback, measurements would not be taken and the sensor assembly could either be repositioned until it is properly seated, or disposed of if defective. While there are a number of sensor products of the general type indicated above currently on the market, none adequately combines ease of use with the protection factors indicated above against measurements being taken with an improperly seated sensor assembly.

SUMMARY OF THE INVENTION

In accordance with the above, this invention provides a pressure sensor assembly and a handle for use therewith, the two combining to form a novel pressure sensor mechanism. In its simplest form, the pressure sensor assembly includes a pair of substrate sections secured together adjacent each other to form the assembly. The substrate sections are preferably flexible. A pressure sensor formed of a pair of electrodes with pressure sensitive material therebetween is formed at the distal end of the assembly. Leads extend from each electrode, which leads are electrically isolated from each other, to a corresponding terminal at the proximal end of the assembly. The assembly is constructed such that electrical contact to all terminals can be made from the same side of the assembly. For preferred embodiments, the assembly also has a third electrode which is electrically connected to one of the other two electrodes by a lead which functions as a sensor-ok lead or trace.

More particularly, for preferred embodiments, the first and second substrate sections are formed on the same substrate which is folded at a point substantially midway between the two sections to bring the two sections adjacent each other. An electrode is formed at the distal end of each of the substrate sections and a layer of pressure sensitive material is provided between the electrodes, by example, by forming a layer of pressure sensitive material over at least one of the electrodes. A lead extends from the electrode on each substrate to a terminal on the substrate, with the leads being on opposite sides of the assembly when the substrates are secured adjacent each other. For a preferred embodiment, when sections are secured together, and in particular when pressure is applied thereto, the lead-terminating terminal on a second of said substrates makes electrical contact with a terminal on a first of the substrates which terminal is connected by a lead to one output terminal on the first substrate. The other output terminal terminates the lead at the same substrate. The two output terminals are thus accessible from the same side of the assembly. A cutaway or window is provided through the second substrate to permit electrical contact to be made with the terminals on the first substrate. A fourth terminal may be provided on the first substrate which is connected by a sensor-ok lead or trace to the lead-terminating output terminal on the first substrate, the sensor-ok trace being used in a manner to be described later to detect and assure good electrical contact between sensor assembly and handle terminals. While for a preferred embodiment only a single sensor is formed at the distal end of the assembly, a plurality of sensors may also be formed at such distal end.

A handle which is adapted for use with one of the pressure sensitive assemblies indicated above includes a circuit board having a pad or terminal corresponding to each terminal on the assembly to which contact can be made from the one side, a slot sized to permit the proximal end of the assembly to fit therein, which slot has guide surfaces to position each terminal of the assembly adjacent the corresponding terminal on the circuit board; a member normally applying pressure to the side of the assembly opposite that containing the exposed terminals when the proximal end of the assembly is in the slot so as to facilitate good electrical contact between the assembly terminals and the corresponding terminals on the board; and a mechanism for permitting the pressure to be released to facilitate insertion and removal of an assembly from the slot. For preferred embodiments, the member for normally applying pressure includes a pivot arm and a means for biasing the pivot arm against the circuit board; and the mechanism for releasing pressure includes a manually operable component for moving the pivot arm away from the board against the bias force. The means for biasing is preferably a spring and the manually operated component preferably includes a second portion of the pivot arm on the opposite side of a pivot element from the pivot arm biased against the board. A button is provided on the second portion which is adapted to have manual pressure applied thereto.

Where the assembly has a sensor-ok trace, the handle may have an electrical control circuit which is connected to receive a first voltage when the terminals on the board which correspond to the terminals on either end of the sensor-ok trace on the assembly are not electrically connected, indicating that an assembly is not properly seated in the slot, and a second voltage when such terminals are electrically connected by the sensor-ok trace, indicating that the assembly is properly seated in the slot. The detection of a properly positioned sensor assembly in the handle may be utilized to trigger a suitable output, for example an audible or visual output, from either the handle or from a computer or other device interfaced to the handle.

The control circuit also detects the resistance of the pressure sensitive material in the sensor element and generates, in response thereto, an output indicative of the pressure applied to the sensor. The handle may be connected to a computer by a cable, may contain a transmitter for sending readings to a corresponding receiver at the computer or other output device, or may include a memory device for storing readings and an output terminal or other suitable output component for facilitating the subsequent downloading of the stored readings to the computer, may provide readings in a suitable manner at the handle, or may otherwise use the readings in various manner.

The foregoing and other objects, features and advantages of the invention will be apparent from the following more particular description of preferred embodiments of the invention as illustrated in the accompanying drawings.

IN THE DRAWINGS

FIGS. 3A and 3B are top views of two sections which may be combined to form a sensor assembly for an alternative embodiment of the invention;

FIG. 6 also illustrates the output cable for the handle;

DETAILED DESCRIPTION

Figures 1A, 1B, 2:
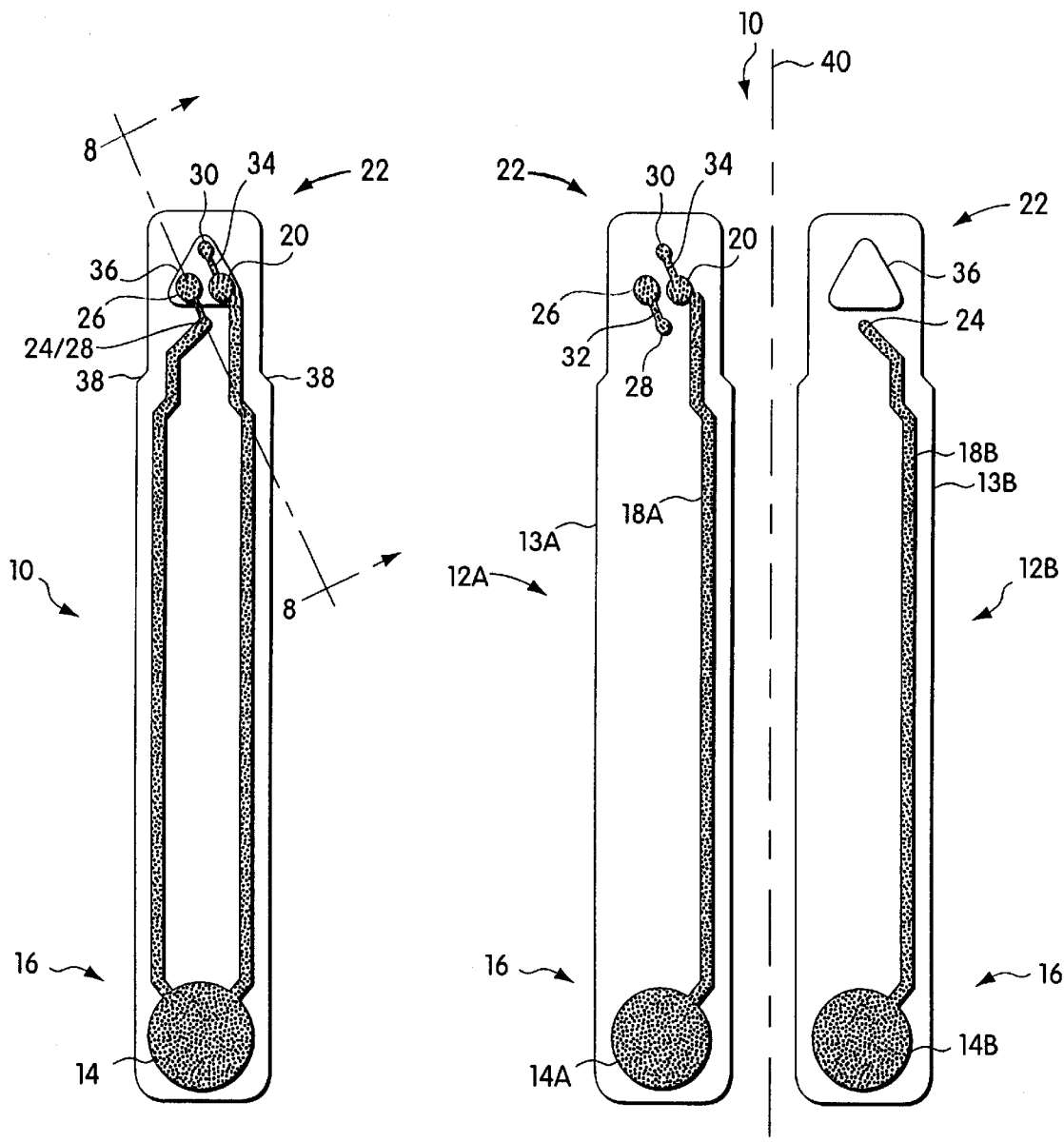
FIGS. 1A and 1B are a top view of the two sections of a sensor assembly before being secured together.
FIG. 2 is a top view of an assembled sensor formed from the two transparent sections shown in FIG. 1A and 1B.

Referring to FIGS. 1A, 1B and FIG. 2, a sensor assembly 10 is shown which is formed of a top sensor assembly section 12A and a bottom sensor assembly section 12B. Section 12A has a top force pad 14A which includes an electrode printed with for example an electrically conductive ink at the distal, force sensing end 16 thereof. Force pad 14A may also have pressure sensitive, variable resistance ink printed over the conductor or electrode. Similarly, the distal or pressure sensing end 16 of section 12B has a bottom force pad 14B printed thereon, which pad includes an electrode formed of an electrically conductive ink and may also include a pressure sensitive variable resistance ink printed over the conductor. While the pressure sensitive ink may be printed on both force pads 14, in accordance with the teachings of the invention, the pressure sensitive ink must be printed on at least one of the force pads. Alternatively, instead of printing pressure sensitive ink on at least one of the electrodes, a pad of pressure sensitive material, in the form, for example of a decal, may be floated or otherwise positioned between the electrodes before the sections 12 are assembled. A conducting trace or lead 18A is formed on substrate 13A which extends along the right side of the substrate from the electrode of force pad 14A to a first output terminal 20 which is also printed on the substrate 13A at the connection or proximal end 22 thereof. Similarly, a connecting trace or lead 18B is printed on and extends along the right side of substrate 13B from the electrode of force pad 14B to a terminal 24 formed at the connection or proximal end 22 of sensor section 12B. Terminals 26, 28 and 30 are also formed at the proximal end of substrate 13A, with terminals 26 and 28 being interconnected by the trace or lead 32 and with terminals 20 and 30 being interconnected by a sensor-ok lead or trace 34.

A window 36 is formed in substrate 13B which window is sized so as to expose terminals 20, 26 and 30 when sections 12A and 12B are assembled as shown in FIG. 2, but not to expose terminals 24 and 28. As may be best seen in FIG. 2, when the two substrate sections are assembled, terminals 24 and 28 will be adjacent each other so that, in conjunction with lead 32, they connect the electrode of force pad 14B to output terminal 26. Electrical connection between terminals 24 and 28 may be made when the sections 12A and 12B are assembled but, for preferred embodiment, as will be discussed later, such connection is made, or at least effectively made, when pressure is applied to the proximal end 22 of the sensor assembly. Sensor assembly has a pair of angled shoulders 38 which, as will be discussed later, are utilized in the proper seating of the assembly in the handle.

While sensor sections 12A and 12B may be formed on separate substrates, for preferred embodiments of the invention, the sensor assembly sections are formed on the same substrate, the sensor assembly being formed by folding the substrate along the line 40 substantially midway between substrate sections 12A and 12B so that the two substrate sections overly each other, with top force sensor pad 14A substantially overlying bottom force sensor pad 14B to form force sensor 14, with leads 18A and 18B extending along opposite sides of the assembly, with the shoulders 38 on both sections overlying each other, with terminals 24 and 28 overlying each other, and with window 36 overlying terminals 20,26 and 30. A suitable adhesive may be applied around the edges of the sections to secure them together or the two sections may be secured together in other manners known in the art.

FIGS. 3A and 3B illustrate an alternative embodiment of the invention which differs from that shown in FIGS. 1A and 1B in that both electrodes 40A and 40B are on the same substrate section 12A' and the connecting traces or leads 18A' and 18B' are formed on the same substrate. Since all of the leads are on the same substrate, terminals 24 and 28 for getting all of the output terminals on the same substrate are not required. Conductive traces 42 are provided between the electrodes 40A and 40B and a pad 44 of pressure sensitive, variable resistance ink is printed on substrate 13B so as to overlie traces 42 and to make contact with electrodes 40 when the sensor is assembled. A window 36' may be provided in substrate 13B to permit electrical contact to be made with terminals 20, 26 and 30, or all of substrate 13B above line 46 may be removed to provide such access. The area exposed at proximal end 22 of section 12A' by window 36' when the two substrate sections are assembled is shown in dotted lines in FIG. 3B. As for the embodiment of FIGS. 1A, 1B and 2, changes in pressure at the distal end 16 of the sensor assembly result in a change in resistance across electrodes 40 which may be detected in a manner to be discussed later, and sensor-ok trace 34 can be utilized in a manner to be described latter to assure that the sensor assembly is suitably seated in its handle.

Figure 4:
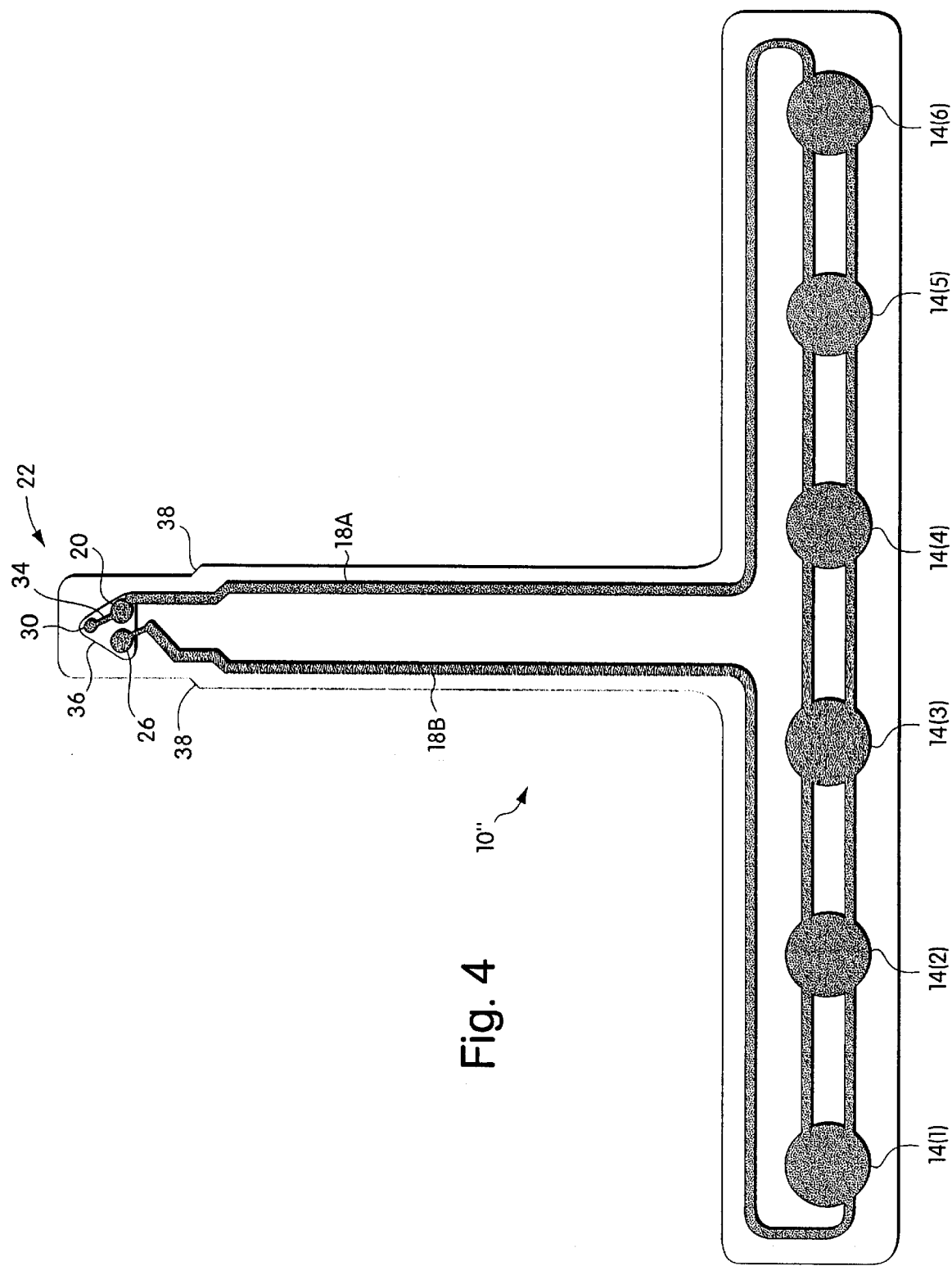
FIG. 4 is a top view of a sensor assembly for still another embodiment of the invention.

FIG. 4 illustrates an embodiment of the invention which differs from those previously shown in that multiple sensors 14(1)–14(6) are provided in sensor assembly 10" rather than only a single sensor. In particular, line 18A is connected in series to one electrode of each of the sensors 14(1)–14(6) while lead 18B is connected in series to the other electrode of each of the sensors. The sensors are thus connected in parallel between leads 18A and 18B. The output from the sensor will thus be indicative of the average resistance of the various sensors, or in other words the average pressure across the sensors, which may be useful in some applications. Further, if the resistance values for the sensors are substantially binary, being high when there is no pressure across the sensor and low when there is pressure across the sensor, the output can be indicative of the number of sensors across which pressure is being applied, although not necessarily of the particular sensor to which pressure is applied. The pressure at each sensor could be determined only by providing a separate output lead and terminal for each sensor, and perhaps a multiplexer in the handle, or by utilizing some other technique to filter, phase shift, delay or otherwise differentiate signals applied to and received from the various sensors so that the pressure at each sensor may be identified.

The proximal or connector end 22 of sensor assembly 10" is the same as that for the sensor assembly 10" of FIG. 2 so that both sensor assemblies will fit in the same handle. Further, while a particular configuration is shown in FIG. 4 for the six sensors, the sensor assembly having a substantially T-shape, this is by no means a limitation on the invention, and the sensor assembly may, for example, have an L-shape, a Y-shape, a Q-shape, or any other shape required for a particular application. Finally, while it has been assumed that substrates 13A and 13B are transparent for FIGS. 2 and 4, so that sensors 14, leads 18, 32 and 34 in the various terminals are visible through the substrate in these figures, if the substrates are opaque, the various sensors, leads, and terminals in these figures would be shown in dotted lines.

Figures 5, 6:
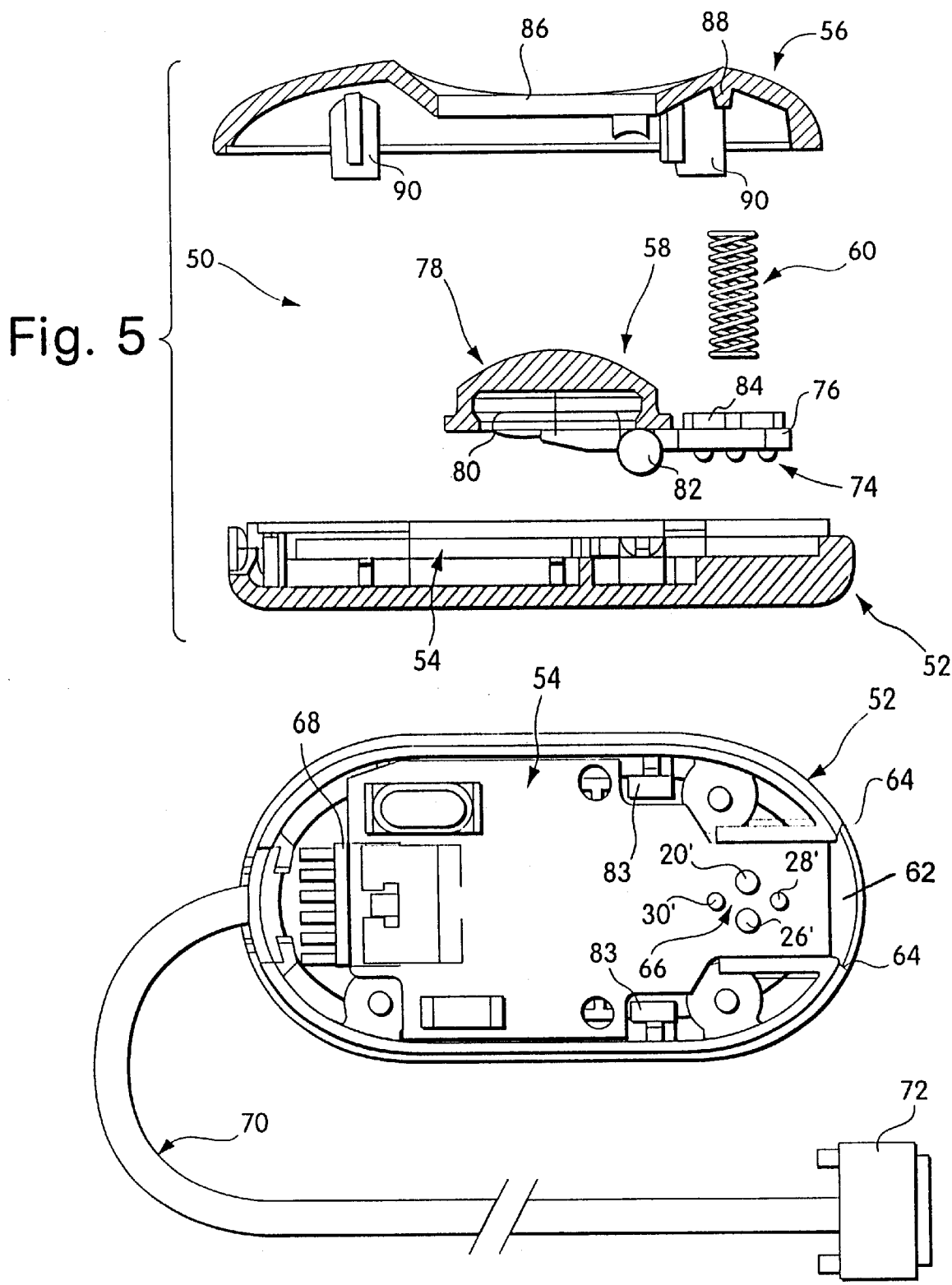
FIG. 5 is an exploded side cutaway view of a handle suitable for use with the sensor assemblies shown in the prior Figures.
FIG. 6 is a top view of the bottom housing, including circuit board, of the handle shown in FIG. 5.
Figure 7A:
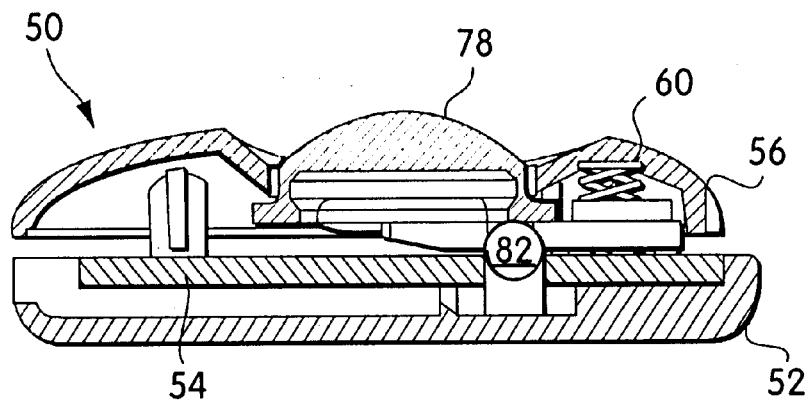
FIGS. 7A, 7B and 7C are side sectional views of an assembled handle with no sensor assembly therein, with a sensor assembly being inserted or removed, and with a sensor assembly supported therein respectively.
Figure 7B:
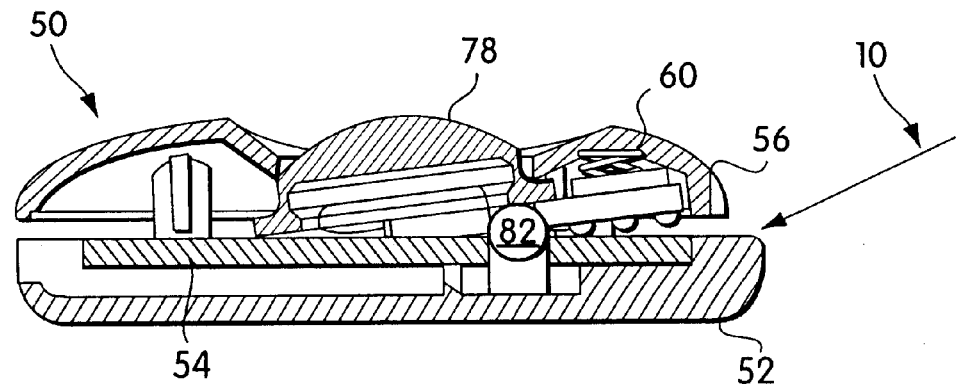

Referring now to FIGS. 5, 6 and 7A, a handle 50 is shown which is suitable for use with any of the sensor assemblies of FIGS. 1A–4. Housing 50 is formed of a bottom housing 52 having a circuit board 54 mounted therein, a top housing 56, a rocker assembly 58, and a spring 60. Bottom housing 52 has a slot 62 formed in its forward end which is sized to permit proximal end 22 of a sensor assembly 10 to fit therein, but not wide enough to permit the passage of shoulders 38 into the slot. Thus, when a sensor assembly is properly positioned in the slot, shoulders 38 of the sensor assembly come to rest against leading edges 64 of the slot. Part of slot 62 may also be formed by a suitable cut-out in top housing 56. Circuit board 54 has a plurality of output circuit connector pads or terminals 66 which pads correspond to the terminals on sensor assembly 10. In particular, pads 20', 26' and 30' make electrical contact with the corresponding terminals on a sensor assembly for transferring electrical signals between the housing and the sensor assembly. Pad 28' does not perform an electrical function but, as will be discussed shortly, is used to assure good electrical contact between terminals 24 and 28 and may in some instances be omitted.

In addition to the circuit connector pads 66, circuit board 54 also has a connector 68 which connects to an output cable 70 extending from the rear of the handle. A jack 72 on the end of the cable may connect to a suitable external input on a computer or other suitable device for receiving the sensor readings. As will be discussed later in conjunction with FIG. 9, board 54 may have a variety of other electrical components mounted thereon which are interconnected in a. suitable manner by traces formed on the circuit board.

Rocker arm 58 has a plurality of pressure fingers 74 on a forward arm 76, there being a pressure finger 74 corresponding to each circuit connector pad 66. Rocker arm 58 also has a button 78 on a rear arm 80 thereof and a pair of pivot rollers 82 (only one of which can be seen in FIG. 5) at the intersection of arms 74 and 80. Rollers 80 rest in corresponding grooves 83 (FIG. 6) in lower housing 52. Spring 60 nests in a guide 84 formed on the top of arm 76. Housing top 56 has an opening 86 through which button 78 projects and a projection 88 which fits in spring 60. Housing top 56 also has a pair of screw assemblies 90 in which two or more screws passing through bottom housing 52 may be secured to hold housing 50 together as shown in FIG. 7A. From FIG. 7A it is seen that when housing 50 is fully assembled, spring 60 is compressed to apply pressure to the top of arm 76 thereby forcing pressure fingers 74 against circuit connect pads 66.

Operation

FIG. 7A shows handle 50 without a sensor assembly 10 mounted therein. When it is desired to mount a sensor assembly 10 in handle 50, the user manually presses button 78, causing rocker arm 58 to rotate in the counterclockwise direction (as viewed in the Figures) against the biasing action of spring 60. This creates a space between pressure fingers 74 and circuit connector pads 66 so that the proximal end 22 of a sensor assembly 10 may be inserted into slot 62 until shoulders 38 abut edges 64 of the slot. With the sensor assembly so positioned in the slot, terminals 20, 24/28, 26 and 30 are adjacent the corresponding circuit connector pads 66 and pressure fingers 74. Once sensor assembly 10 is seated in handle 50, the user releases button 78, permitting spring 60 to return rocker arm 58 to its initial position as shown in FIG. 7C.

Figure 7C:
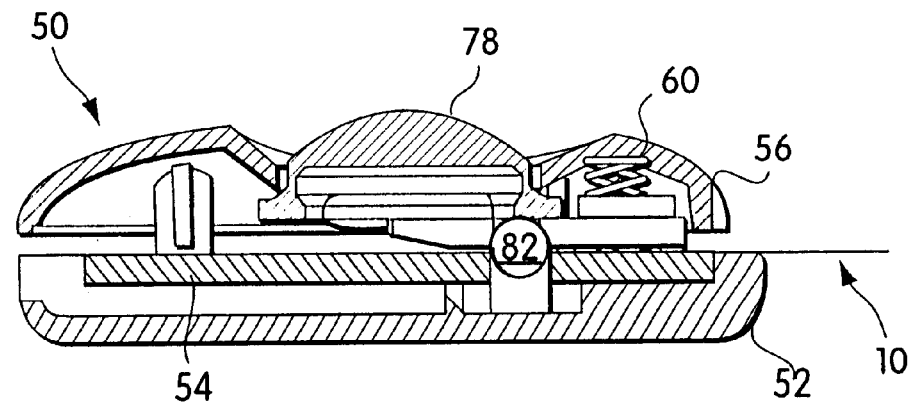
Figure 8:
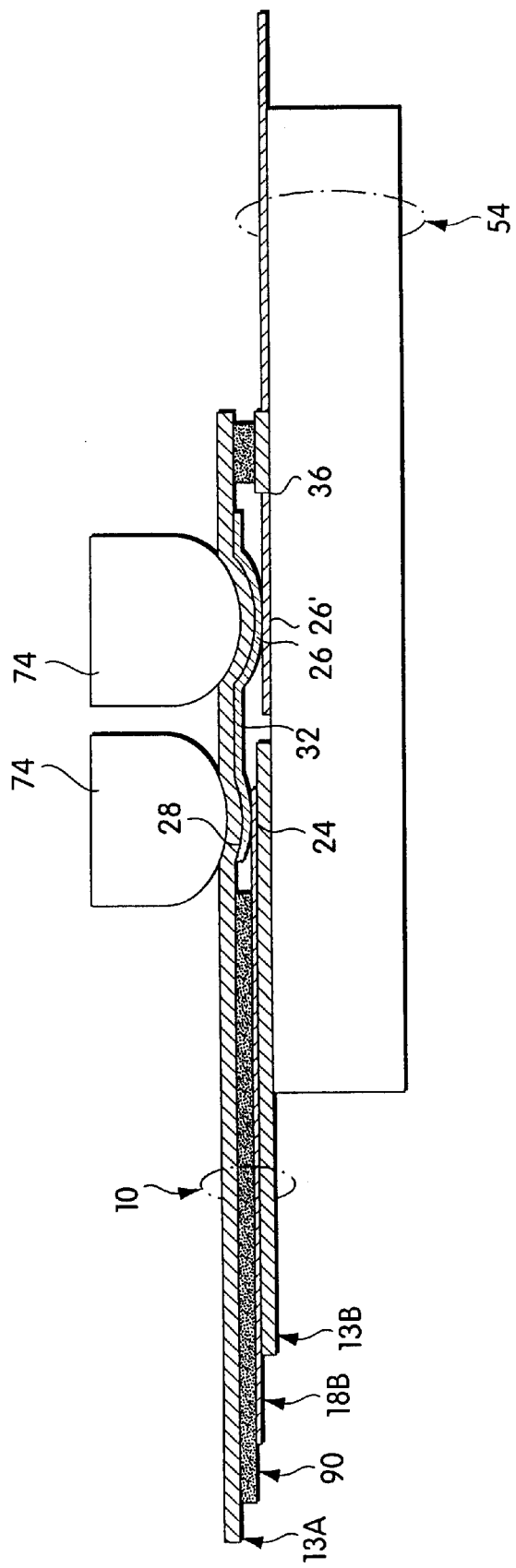
FIG. 8 is an enlarged sectional view taken along the line 8—8 in FIG. 2 of a portion of the handle with the proximal end of the sensor assembly mounted therein.

FIG. 8 is an enlargement of the contact portion of FIG. 7C taken at the angle shown in FIG. 2 and illustrating how one of the pressure fingers presses terminals 24 and 28 together to connect pressure pad 14B and the electrode thereof to output terminal 26 through lead 32, and how another of the pressure fingers presses terminal 26 through window 36 against circuit connector pad 26' to make one of the three required electrical connections between the sensor assembly and the circuit board. The other two electrical connections for terminals 20 and 30 with corresponding circuit connector pads 20' and 30' are similarly made. When a sensor assembly is to be removed from handle 50, the process described above is reversed. Namely, button 78 is manually pressed to release the pressure being applied to proximal end 22 of sensor assembly 10, permitting the sensor assembly to be easily removed from the handle. Button 78 may then be released to return the handle to the condition shown in FIG. 7A.

Figure 9:
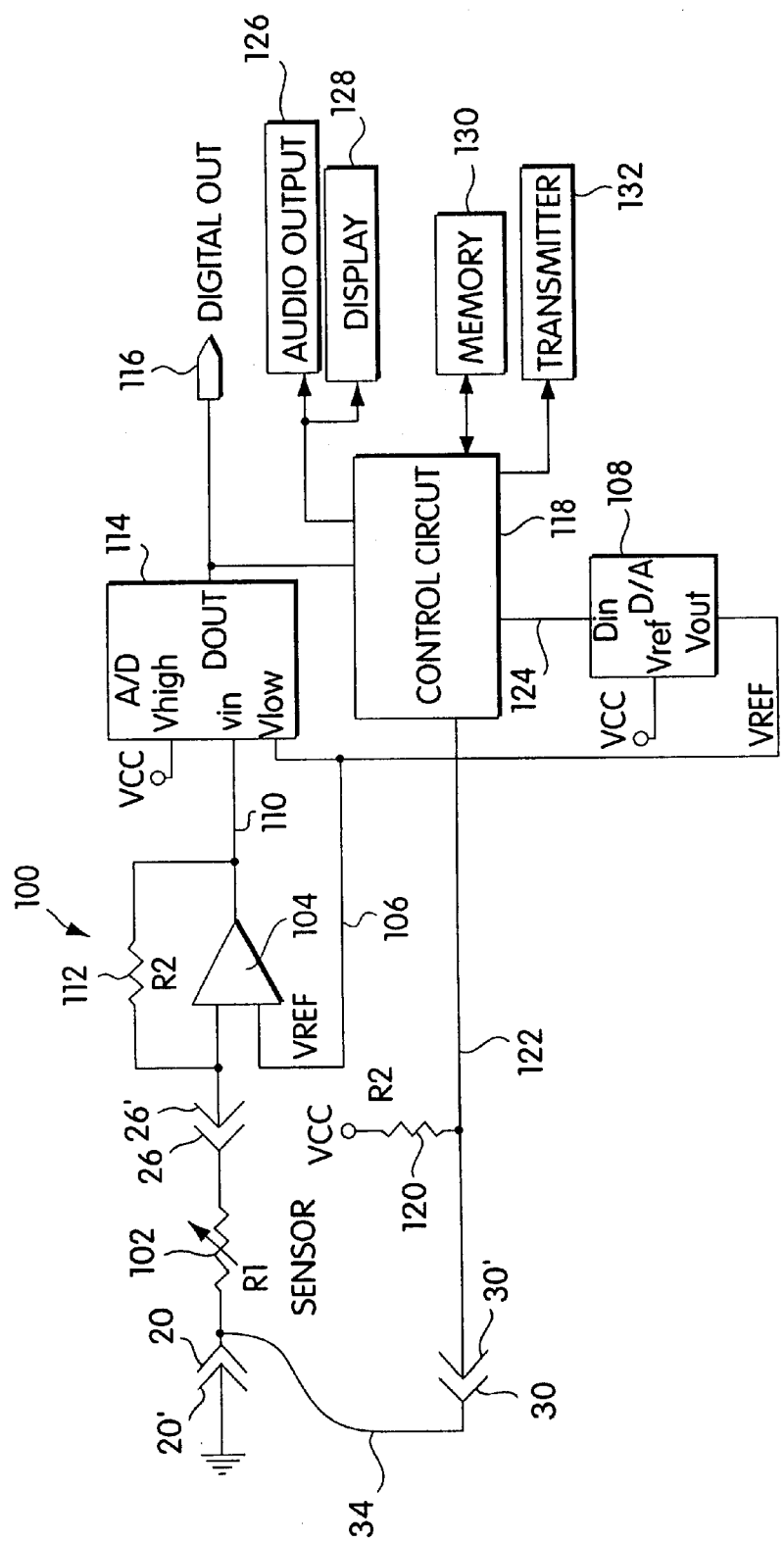
FIG. 9 is a schematic block diagram of an exemplary circuit for use in the handle.

FIG. 9 shows an electronic circuit 100 which may be used in handle 50. Referring to FIG. 9, it is seen that the variable resistance 102 of sensor 14 is connected between circuit contact pad 20', which is in turn connected to ground, and circuit contact pad 26', while sensor-ok trace 34 is connected between grounded circuit connector pad 20' and circuit connector pad 30'. Connector pad 26' is connected to one input of an operational amplifier 104, the other input to which is a reference voltage on line 106 from D/A converter 108. Output line 110 from op amp 104 is fed back through resistor 112 as an input to the op amp and is also connected as the input to A/D converter 114. A reference voltage Vcc is connected to the Vhi input of converter 114 and the reference voltage on line 106 is connected to the Vlow input of the converter. The output from converter 114 is connected to a digital output terminal 116 from the circuit and is also connected as an input to a control circuit 118. Control voltage Vcc is also applied through a resistor 120 to line 122, which line is connected both to circuit connector pad 30' and to an input of control circuit 118. The Din input to D/A converter 108 is from control circuit 118 over line 124 and control voltage Vcc is applied as the reference input to this converter.

There are also four optional components shown as connected to control circuit 118. These components are an audio output component 126, a display 128, a memory 130 and a transmitter 132. An input, such as a keypad, may also be provided. Audio output 126 may for example generate a beep or other suitable sound under circumstances to be described later or ma;y provide an audio indication of measured values. Display 128 may for example be a standard LCD display or other suitable display for providing measurement values. Memory 130 may be a suitable semiconductor memory in which measurements may be stored for subsequent use and transmitter 132 may be a standard RF transmitter chip or other suitable circuit.

In operation, when a sensor assembly 10 is not positioned in handle 50, there is substantially no current flow through resistor 120 and line 122 is at a potential which is substantially equal to Vcc. Control circuit 118 is programmed to interpret a Vcc potential on line 22 as an indication that a sensor assembly is not in the handle, or is at least not properly positioned in the handle.

When a sensor assembly 10 is mounted in handle 50 and good electrical contact is made between terminals 20 and 30 on the sensor assembly and corresponding pads 20', 30' on board 54 in the handle, ground potential is applied to line 122. Control circuit 118 is programmed to recognize a ground potential on line 122 as an indication that the sensor assembly is properly positioned in the handle and good electrical contact is being made between all of the assembly terminals and the corresponding circuit board pads. Note that even though sensor-ok trace 34 only assures good electrical contact between two of the terminal/pad combinations, if good electrical contact has been made at two points, it can be assumed that good electrical contact is being made at all of the terminal/pad junctions. Resistor 120 preferably has a relatively high resistance value, for example 100k ohms to approximately 1 meg ohm, so as to minimize current flow therethrough and to thus minimize the energy drain caused by sensor-ok detection during measurements. Alternatively, some mechanism may be provided to prevent current flow through, resistor 120 once a sensor-ok determination has been made.

Control circuit 118 may be programmed to respond to a sensor-ok determination by providing some feedback of this fact to the user. For example, display 128 may be or may include a low energy lamp which is illuminated by control circuit 118 when a sensor-ok indication is received. Alternatively, resistor 120 may for example be a lamp which is illuminated when there is current flowing therethrough. For this embodiment, it may not be necessary to connect line 122 to the control circuit, although it is preferable that information on the proper positioning of the sensor also be provided to the control circuit. However, since a lamp represents an energy drain from the handle, it may be preferable for control circuit 118 to operate audio output device 126 to for example generate a selected audio output, for example one or more beeps, when a sensor-ok determination is made. Another option would be for the control circuit to provide an output through terminal 116 and cable 70 to the computer (not shown) indicating that the sensor is properly positioned; the computer generating a suitable visual or audio feedback to the user in response to this output. Other indications known in the art could be provided to the user of a sensor-ok condition.

If a sensor assembly 10 has been placed in handle 50, but is not properly seated so that good electrical contact is not being made at each of the terminal/pad junctions, a potential other than ground will appear on line 122, and anything other than a solid ground on line 122 will not be interpreted by the control circuit as a sensor-ok indication. The reason for is this that terminal is significantly smaller than terminals 20 and 26, and the same is true for the corresponding pads on board 52. Therefore, if good electrical contact does not exist for the output terminal 20, 26/pad 20', 26' pairs, there should be no electrical contact for the terminal 30/pad 30' pair, resulting in ground potential not appearing on line 122.

The sensitivity of the sensor is controlled in a manner described in some detail in copending application Ser. No. 08/898,366 which is assigned to the assignee of this application. In particular, the control circuit generates a digital output which is related to required sensitivity on lines 124, which sensitivity value is converted to an analog Vref signal on line 106. A higher reference voltage to op AMP 104 results in greater sensitivity to small variations in pressure sensitive variable resistance 102, while a lower Vref results in the circuit covering a greater range of variations in resistance 102, but with less sensitivity. The voltage outputted from op amp 104 may be digitized in A/D converter 114 and applied directly through cable 70 to an output computer and/or may be applied to circuit 118, either for further processing or for other reasons. Op amp 104 provides some amplification of a signal indicative of variable resistor 102, and thus of pressure, and additional amplification may be provided in the circuit if needed.

Instead of a digital output from converter 114 being applied directly to a cable 70, where greater mobility of operation is required, the output from converter 114 may be provided through control circuit 118 to a transmitter 132 for transmission to a corresponding receiver at a computer or other suitable utilization location. Readings provided to control circuit 118 may also be stored in memory 130 and may be subsequently downloaded from the memory by a variety of techniques known in the art. It is also possible to provide for example an LCD display on the handle, for example display 128, on which control 118 would cause measurements to be displayed for reading by a user. Control 118 could also cause readings to be outputted audibly through an audio output 126. Other means for utilizing readings outputted from A/D converter 114 known in the art could also be utilized.

While a variety of output devices have been shown in FIG. 9, it is unlikely that all such devices would be used in a single handle 50, a transmitter for example not being provided if a memory 130 is utilized, and a display 128 possibly not being utilized if either a memory or transmitter is utilized. Similarly, while ground and Vcc have been shown as being applied at various points in the circuit, this is not a limitation on the invention, and the places where these potentials are applied could for example be reversed. Further, all that is required is that these two potentials be different, so that Vcc could be either positive or negative and the second potential need not be ground. Similarly, while several variations in the sensor assembly have been discussed above, other variations which achieve the same objectives are also possible.

Considering the handle, while a coil spring 60 is shown in the Figures for biasing rocker assembly 58, other types of springs or other biasing components might be utilized to cause pressure to be applied by pressure fingers 74, and these biasing components could be located as shown to press down on the top of arm 76, or could also be located to press up on the underside of arm 80, to pull up on the top of arm 80 or to pull down on the bottom of arm 76. However, the location shown in the Figures is the currently preferred location for the biasing element. Other variations in the configuration of the handle are also possible including using a spring-loaded catch and release mechanism similar to that employed in click-top pens or a cammed plunger in lieu of rocker arm 58 to apply bias pressure.

Thus, while the invention has been particularly shown and described above with reference to preferred embodiments, the foregoing and other changes and form and detail may be made therein by those skilled in the art without departing from the spirit and scope of the invention.

What is claimed is:

1. A pressure sensor assembly including:
   first and second substrate sections;
   a first and a second pressure sensor electrode formed at a distal end of said first and second substrate sections respectively;
   a layer of a pressure sensitive material over at least one of said electrodes;
   a first, a second, and a third terminal at a proximal end of said first substrate section and a fourth terminal at a proximal end of said second substrate section;
   first and second leads on said first substrate section, said first lead electrically connecting said first and second terminals, and said second lead electrically connecting said first electrode and said third terminal;
   a third lead on said second substrate section which electrically connects said second electrode and said fourth terminal; and
   a window formed at the proximal end of said second substrate section;
   said first and second substrate sections being secured together adjacent each other, said electrodes, terminals, leads and window being arranged on their respective substrate sections such that when the substrate sections are secured together, said first and second electrodes are adjacent, with said pressure sensitive material therebetween to form a pressure sensor, said second and third leads are on opposite sides of the assembly so as not to contact each other, said first and fourth terminals are adjacent each other, and said window overlies said second and third terminals to permit electrical contact to be made with these terminals through said second substrate.

2. An assembly as claimed in claim 1 where said first and second substrate sections are sections of a single substrate, said substrate being folded at a point substantially mid-way between the substrate sections to bring the sections adjacent for securing together.

3. An assembly as claimed in claim 1 including a fifth terminal on said first substrate section, and a fourth lead electrically connecting said third and fifth terminals, said window also overlying said fifth terminal to permit electrical contact to be made thereto through said second substrate section.

4. An assembly as claimed in claim 3, wherein said fifth terminal is substantially smaller than said second and third terminals.

5. A pressure sensor assembly including:
   first and second substrate sections secured together adjacent each other to form said assembly;
   a pressure sensor at a distal end of said assembly, said sensor including an electrode on each said substrate section positioned adjacent each other with a layer of pressure sensitive material therebetween;
   a lead extending from each said electrode along the corresponding substrate section to a proximal end of the assembly, the leads being adjacent to and electrically isolated from each other;
   first and second output terminals at the proximal end of said first substrate section, which output terminals are exposed to permit electrical contact to be made therewith, one of said output terminals being at the proximal end of the lead on the first substrate section; and
   a mechanism operative when the substrate sections are secured together for electrically connecting the proximal end of the lead on the second substrate section to the second output terminal.

6. An assembly as claimed in claim 5 including a sensor ok trace on said first substrate section which is connected at one end to one of the output terminals on said first substrate section and at its other end to a third terminal on said first substrate section.

7. An assembly as claimed in claim 6 wherein said means for electrically connecting includes a fourth terminal on said first substrate section which is electrically connected to said second terminal and electrically connectable to the proximal end of the lead for the second substrate section, and a window provided in the proximal end of the second substrate section which window overlies the first, second and third terminals on said first substrate section.

8. An assembly as claimed in claim 5 wherein there are a plurality of said pressure sensors at the distal end of said assembly, said leads being connected to each said pressure sensor.

9. A pressure sensor assembly including:

first and second substrate sections secured together adjacent each other;

a sensor, including a first and a second electrode having pressure sensitive material therebetween, at a distal end of said substrates; and first, second and third terminals at a proximal end of said substrate sections, said first and second terminals being electrically connected to said first and second electrodes respectively by leads which are electrically isolated from each other, and said second and third terminals being electrically connected by a lead which functions as a sensor-ok trace.

10. An assembly as claimed in claim 9, wherein said third terminal is substantially smaller than said first and second terminals.

* * * * *